United States Patent
Yan et al.

(10) Patent No.: US 11,858,867 B2
(45) Date of Patent: Jan. 2, 2024

(54) DENTAL ZIRCONIA TREATMENT TECHNOLOGY

(71) Applicant: ChengDu Besmile Medical Technology Corp. Ltd., Chengdu (CN)

(72) Inventors: Xinzhang Yan, Chengdu (CN); Jiao Li, Chengdu (CN); Qin Ma, Chengdu (CN); Moushan Liu, Chengdu (CN); Dan Wu, Chengdu (CN); Shuai Liu, Chengdu (CN)

(73) Assignee: Chengdu Besmile Medical Technology Corp. Ltd., Chengdu (CN)

(*) Notice: Subject to any disclaimer, the term of this patent is extended or adjusted under 35 U.S.C. 154(b) by 252 days.

(21) Appl. No.: 17/388,007

(22) Filed: Jul. 29, 2021

(65) Prior Publication Data

US 2021/0355042 A1    Nov. 18, 2021

Related U.S. Application Data

(63) Continuation of application No. PCT/CN2019/084893, filed on Apr. 29, 2019.

(30) Foreign Application Priority Data

Jan. 30, 2019   (CN) .......................... 201910092490.5

(51) Int. Cl.
```
C04B 41/50     (2006.01)
A61K 6/818     (2020.01)
A61C 13/08     (2006.01)
C04B 35/48     (2006.01)
C04B 41/00     (2006.01)
C04B 41/45     (2006.01)
C04B 41/87     (2006.01)
```

(52) U.S. Cl.
CPC ........ *C04B 41/5045* (2013.01); *A61C 13/082* (2013.01); *A61K 6/818* (2020.01); *C04B 35/48* (2013.01); *C04B 41/009* (2013.01); *C04B 41/0072* (2013.01); *C04B 41/4539* (2013.01); *C04B 41/87* (2013.01); *C04B 2235/3244* (2013.01)

(58) Field of Classification Search
CPC ............................ C04B 41/5045; C04B 41/85
See application file for complete search history.

(56) References Cited

U.S. PATENT DOCUMENTS

| | | | | |
|---|---|---|---|---|
| 2010/0221683 | A1* | 9/2010 | Franke | C04B 41/85 252/182.34 |
| 2011/0306017 | A1* | 12/2011 | Tanaka | C04B 41/85 433/203.1 |
| 2018/0235847 | A1 | 8/2018 | Balasubramanian et al. | |

FOREIGN PATENT DOCUMENTS

| | | |
|---|---|---|
| CN | 103622837 A | 3/2014 |
| CN | 105854080 A | 8/2016 |
| CN | 105963035 A | 9/2016 |
| CN | 109608233 A | 4/2019 |

OTHER PUBLICATIONS

International Search Report; International Searching Authority/CN dated Sep. 10, 2019; International Application No. PCT/CN2019/084893; 4 pgs.; National Intellectual Property Administration, PRC (ISA/CN); Beijing, China.

* cited by examiner

*Primary Examiner* — Dah-Wei D. Yuan
*Assistant Examiner* — Andrew J Bowman
(74) *Attorney, Agent, or Firm* — Andrew D. Fortney; Central California IP Group, P.C.

(57) ABSTRACT

The present disclosure relates to the field of dental material treatment, and particularly to a dental zirconia treatment technology. The specific technical solution is as follows: a zirconia treatment method, mainly involving color masking the zirconia, surface roughening the zirconia, coloring the zirconia, surface protection treatment and additional protective film treatment. Based on this treatment method, a brand-new color masking liquid, coloring liquid and adhesive solution are proposed. The present zirconia treatment technology not only meets the individualized requirements of patients for teeth, but also meets the requirements of dentists for convenient operation, so that it is of great value in application and popularization on the market.

20 Claims, No Drawings

DENTAL ZIRCONIA TREATMENT TECHNOLOGY

TECHNICAL FIELD

The present disclosure belongs to the field of dental material treatment, and particularly relates to a dental zirconia treatment technology.

BACKGROUND

Zirconia is a composite material widely used in the field of dental restoration, and has excellent mechanical properties. However, in the process of denture restoration, in addition to having excellent properties, the materials need to be endowed with the aesthetic effect of being highly close to natural teeth.

People's pursuit of the aesthetic effect of dentures makes it difficult to solve at least the following two difficulties when zirconia is made into dentures. (1) When used to make the upper prosthesis of implant dentures, zirconia is required not only to have good translucency, but also to have a certain masking effect, so as to avoid exposing the metal color of the implant abutment and affecting the aesthetic. However, there is a certain contradiction between translucency and masking effect, which is difficult to solve. (2) Even if zirconia with excellent translucency and color masking performance can be obtained, it cannot be directly used as the implant. This is because, although the color of patients' teeth seems to be only yellow and white, in practice, there are often various intermediate colors and special colors, for example, the teeth of people who often smoke may be brown or even black. If the implanted teeth are not colored according to the actual color of patient's teeth, the implanted teeth will look very incongruous. However, if coloring is carried on site against the actual color of patient's teeth, there are some problems such as troublesome operation and long coloring time. In addition, when zirconia is colored, there are still some gaps on its surface, which easily makes bacteria and other substances penetrate into the gaps, affecting the service life of dentures and even bringing new oral health problems to patients.

To solve the problem (1), the existing general solution is as follows: zirconia with low translucency is selected as the base, and then a ceramic veneer is added on the surface to cover the metal with the ceramic veneer. However, it is not only cumbersome and costly, but also needs to consider the bonding between the zirconia and the ceramic veneer, and also needs to adjust the color of the ceramic veneer, which is very troublesome. Zirconia with high translucency is also selected as the base in the art, and after the base is completed, it is painted with a color masking material to achieve the effect of color masking. However, if the color masking material is painted too thick, it will affect the aesthetic, and if too thin, it will be difficult to achieve a good masking effect, that is to say, it is difficult to accurately apply the painting technique. In addition, the bonding between the color masking material and the zirconia should be considered. More importantly, whether it is ceramic veneering or painting, it needs to add a layer of material outside the zirconia base, which occupies a certain space. For products with high requirements on dimensional accuracy, such as dentures, if the increased space is considered, it will greatly increase the difficulty and cost of production; and if the increased space is not considered, it will affect the installation and use of dentures.

In order to solve the problem (2), dentures with 16 or 26 shades of color are prepared with reference to VITA color shade guide in advance, and selected according to the needs of patients when using them. However, these colors are based on yellow, red and gray, and as mentioned above, many patients' teeth are not limited to these colors. If the pre-prepared dentures are used directly, it is difficult to meet today's personalized needs.

Therefore, it is of great practical significance to provide an all-around technology for treatment of dental zirconia, which not only meets the individualized needs of patients for dental aesthetic, but also meets the needs of dentists for convenient operation.

SUMMARY

The objective of the present disclosure is to provide a technology for all-around treatment of dental zirconia.

In order to realize the objective of the present disclosure, the technical solution adopted by the present disclosure is as follows: a zirconia treatment method, comprising the following steps:
(1) color masking a zirconia ceramic prepared by pre-sintering zirconia powder;
(2) coloring the zirconia ceramic;
(3) carrying out surface protection treatment on the zirconia ceramic;
wherein color masking comprises painting a color masking liquid on or over a surface of the pre-sintered zirconia ceramic, oven-drying the painted zirconia ceramic, then sintering the dried, painted zirconia ceramic.

Preferably, the color masking liquid has a formula comprising, in mass percentages, 95-98% of a mother liquor, 1.3-1.6% of an alcohol, 0.03-3.40% of potassium nitrate, 0.1-0.3% of yttrium chloride and 0.3-0.4% of citric acid; and the mother liquor has a formula comprising, in mass percentages, 18-23% of ethylene glycol, 1-5% of gluconic acid, 1-3% of citric acid, 1-3% of praseodymium nitrate, and water. For example, the balance of the mother liquor (other than the ethylene glycol, the gluconic acid, the citric acid, and the praseodymium nitrate) may be water, which may be distilled and/or deionized water.

Preferably, sintering is carried out at 1530° C. for 2 h.

Preferably, the zirconia ceramic is colored with a first coloring liquid comprising, in mass percentages, 0.01-26% of a first coloring agent, 0.2-35% of a first dispersant and 60-97% of a first solvent.

Preferably, the first coloring agent is at least one of erbium chloride, ferric chloride and manganese nitrate; and/or the first dispersant is polyethylene glycol.

Preferably, the mass percentage of the polyethylene glycol is 10%.

Preferably, the first coloring agent comprises erbium chloride, ferric chloride and manganese nitrate, in mass percentages of 0.5-13%, 0.5-6% and 0.01-6%, respectively.

Alternatively, the zirconia ceramic is colored with a second coloring liquid comprising, by mass percentages, 0.01-48% of a second coloring agent, 0.1-5% of a second dispersant, 0.05-2% of a complexing agent and 45-99% of a second solvent.

Preferably, the second coloring agent is one or a mixture of two or more of erbium chloride, ferric chloride, neodymium nitrate, manganese nitrate, ammonium metavanadate, cerium nitrate, praseodymium nitrate, cobalt nitrate and nickel nitrate; and/or the second dispersant is any one of polyethylene glycol, polyacrylic acid or polyurethane; and/ or the complexing agent is any one of citric acid, glucose, ethylenediaminetetraacetic acid, sodium citrate or 2,3-dimercaptosuccinic acid.

Preferably, the surface protection treatment in step (3) comprises using an adhesive solution comprising, in parts by mass, 40-100 parts of a matrix, 2-6 parts of a diluent, 3-5 parts of an adhesive monomer, 6-15 parts of a polymerization inhibitor, 30-55 parts of carbon nanotubes, 20-60 parts of a filler, 1-8 parts of tartaric acid and 30-70 parts of water.

Preferably, coloring and carrying out the surface protection treatment are performed simultaneously, and using the adhesive solution comprises mixing the coloring liquid with the adhesive solution to obtain a mixed solution, painting the mixed solution on or over the surface of the zirconia ceramic, and crystallizing the painted zirconia ceramic at a high temperature. Alternatively, using the adhesive solution comprises painting the adhesive solution on or over the surface of the zirconia ceramic after coloring the zirconia ceramic, and then drying the painted, colored zirconia ceramic.

Preferably, the diluent is a methacrylate monomer (e.g., of the formula $[H_2C=C(CH_3)-C(=O)-O-R$, where R is H, an alkali metal, or a $C_1$-$C_6$ alkyl group]) or an oligomer or polymer thereof (e.g., of the formula $R'-[-H_2C-C(CH_3)(C[=O]-O-R)-]_n-R''$, where n is an integer of 2-10,000, each R is independently as described for the monomer, and R' and R'' are conventional end groups for methacrylate oligomers or polymers; and/or the adhesive monomer is 4-methacryloyloxyethyl trimellitic anhydride; and/or the polymerization inhibitor is one or a mixture of two or more of tert-butyl hydroquinone, hydroquinone and p-tert-butyl catechol.

Preferably, the filler is a mixture of two or more of silicon dioxide, aluminum oxide, calcium fluoride and titanium dioxide.

Preferably, the filler is made by melting the mixture of two or more of silicon dioxide, aluminum oxide, calcium fluoride and titanium dioxide, quenching the melted mixture, and then crushing the quenched mixture to a particle size smaller than that of the carbon nanotubes.

Preferably, the method further comprises surface roughening the zirconia ceramic before coloring the zirconia ceramic and after color masking the zirconia ceramic. For example, surface roughening may comprise the following steps:

(1) sandblasting the zirconia ceramic using 30-60 μm zirconia powder for 5-10 s under a pressure of 0.2-0.3 MPa; and then washing the sandblasted zirconia ceramic 3-5 times with deionized water;

(2) mixing hydrochloric acid and nitric acid, wherein the hydrochloric acid has a concentration of 1-2 mol/L, the nitric acid has a concentration of 1-2 mol/L, and the volume ratio of hydrochloric acid to nitric acid is 1:2-3; heating the mixture of hydrochloric acid and nitric acid to 70-80° C. to obtain a mixed acid solution; and soaking the sandblasted zirconia ceramic in the mixed acid solution for 10-15 min; and (3) washing the zirconia ceramic 3-5 times with deionized water.

Preferably, the method further comprises forming a protective film on or over the surface of the zirconia ceramic after the surface protection treatment. For example, forming the protective film may comprise painting a layer of a silane coupling agent on or over the surface of the zirconia ceramic, and then drying the painted zirconia ceramic.

The present disclosure has the following beneficial effects.

(1) The present disclosure provides a complete and all-around treatment technology for zirconia bases (e.g., ceramics, including initially sintered and/or fully sintered ceramics). The treatment technology of the present disclosure can meet not only the individualized requirements of patients for teeth, but also the requirements of dentists for convenient operation.

(2) In the first step of the technical solution of the present disclosure, the present disclosure first provides a brand-new idea to solve the contradiction between the translucency and color masking property of zirconia: instead of veneering/painting the prepared (e.g., fully sintered) zirconia, the zirconia ceramic that has not been secondarily sintered (e.g., pressed and pre-sintered at a relatively low temperature, such as ≤1100° C., but not sintered a second time at a relatively high temperature, such as ≥1500° C.) are treated with a color masking liquid, and then the zirconia ceramic with the color masking liquid are secondarily sintered, so that the components of the color masking liquid react and crystallize together with the zirconia ceramic to become a part of the sintered zirconia ceramic. The color masking liquid is closely bound to the ceramic while not increasing the thickness of the ceramic, achieving a good balance between translucency and masking effect.

(3) After obtaining the zirconia base with excellent translucency and color masking property, how to make the zirconia base adapt to the tooth color of patients while facilitating operation by dentists is the second difficult problem solved by the present disclosure. According to the present disclosure, firstly, the surface of the zirconia ceramic is roughened. By adjusting the parameters of the surface roughening in conjunction with adjustment of the polyethylene glycol content in the coloring liquid, when the polyethylene glycol content reaches (or is) 10%, the color of the zirconia denture will not change as long as the coloring time is over 15 s, nor will it deepen with a longer coloring time. As such, in actual operation, even if the dentist does not precisely control the coloring time, an ideal tooth color can be obtained.

(4) The present disclosure also provides an adhesive solution, which can be mixed with the coloring liquid or used after coloring. After coloring, there may still be some large pores on the surface of the zirconia, and bacteria, acids, enzymes and products thereof in the mouth can penetrate into the pores, thus causing oral infections and/or other hazards. The adhesive solution can form a protective film on or over the surface of the zirconia ceramic to reduce the occurrence of such hazards.

Specifically, the adhesive solution works as follows. To prepare the adhesive solution, firstly a filler is dispersed in the reaction system, then carbon nanotubes are added thereto, so that the carbon nanotubes adhere with the filler and the reaction solution both inside and outside of the carbon nanotubes to form scaffolds in the pores on the surface of the zirconia ceramic with the carbon nanotubes as bridges. Meanwhile, the adhesive solution (when mixed and used together with the coloring liquid, the adhesive solution also contains the coloring liquid at this time) outside the carbon nanotubes adheres to the inner wall of the pores, thus increasing the adhesive strength between the coloring liquid containing the adhesive solution and the zirconia ceramic. The roughening treatment of the zirconia surface makes it easier for the coloring liquid containing the adhesive solution to be adsorbed in the pores, and also makes it easier for the carbon nanotubes to form bridges in the pores.

DETAILED DESCRIPTION

1. The first step of treating dental zirconia in the present disclosure is to solve the contradiction between the translucency and masking property of the zirconia base, which is specifically implemented as follows.

The present disclosure provides a product for improving/balancing the translucency and masking property of dental zirconia ceramics (hereinafter referred to as color masking liquid), which has a formula comprising, in mass percentages, 95-98% of a mother liquor, 1.3-1.6% of an alcohol (e.g., a $C_1$-$C_4$ alkanol such as methanol or ethanol, or a $C_2$-$C_4$ alkanediol such as ethylene glycol or propylene glycol), 0.03-3.40% of potassium nitrate, 0.1-0.3% of yttrium chloride and 0.3-0.4% of citric acid.

The formula of the mother liquor comprises, in mass percentages, 18-23% of ethylene glycol, 1-5% of gluconic acid, 1-3% of citric acid, 1-3% of praseodymium nitrate, and water. For example, the balance of the mother liquor (e.g., other than the ethylene glycol, the gluconic acid, the citric acid, and the praseodymium nitrate) may comprise of consist essentially of water, which may be distilled and/or deionized water.

Among them, the potassium nitrate can make the zirconia base and/or the masking layer have a milky color after sintering, so as to achieve the color masking effect. As the concentration of potassium nitrate increases, generally speaking, the masking effect will also enhance. The alcohol acts as a dispersant because of its good compatibility. The yttrium chloride acts as a catalyst.

All components of the color masking liquid except the mother liquor are accurately weighed, and preliminarily mixed at room temperature. Then, the mother liquor is added thereto, the mixture is well stirred to dissolve the components and obtain the desired color masking liquid.

To prepare the zirconia ceramic, pressing and pre-sintering are carried out first for preliminary forming and preliminary crystallization, and then secondary sintering is carried out to improve the density and mechanical strength of the zirconia ceramic. The preliminary pressing, pre-sintering and other processes can be carried out conventionally. The color masking liquid is used in the secondary sintering after the pre-sintering. Specifically, the color masking liquid is painted on or over the surface of the pre-sintered zirconia ceramics. The amount of the color masking liquid on or over the surface of a single denture (e.g., a single tooth) is less than or equal to 0.001 g, and in practice, a little color masking liquid is taken by dipping to paint the zirconia without repeating the painting step. The painting may be repeated up to two times. Then, the zirconia ceramics are put into an oven for drying at 90° C., and half an hour later, taken out and put into a crucible with zirconium beads. The crucible is then put into a sintering furnace, the temperature curve of the sintering furnace is set, and the crucible is then kept at 1530° C. for 2 h to allow the color masking liquid and zirconia ceramics to undergo secondary sintering together.

Before the zirconia base is preliminarily formed (pre-sintering is completed, but secondary sintering has not yet been performed), the color masking liquid is painted on or over the zirconia base, which is then subjected to the secondary sintering process, so that the color masking liquid reacts and crystallizes with the zirconia base, and the zirconia base is directly colored by the color masking liquid, making the color masking layer become a part of the zirconia base and constitute a built-in color of the base. The color masking layer is closely bound to the base after reaction, which does not increase the volume of the base.

The present disclosure will be further explained with specific examples below.

Example 1: Effect of Formula of Color Masking Liquid

1. Nine groups of color masking liquids were prepared by the above method, wherein the formula of these group of color masking liquids comprises 96.83% of a mother liquor, 1.52% of ethanol, 1.1% of potassium nitrate, 0.2% of yttrium chloride and 0.35% of citric acid. The formula of the mother liquor is shown in Table 1, wherein the numerals in the table indicate the mass percentages of the corresponding components in the color masking liquid, and the balance is deionized water, with the sum of all the components being 100%.

The zirconia powder used in this example was purchased from Shanghai Linghao Metal Material Co., Ltd., with an article number of ZR-2. The zirconia powder was isostatically pressed at 150 MPa for 10 min (e.g., to form a pressed or "green" zirconia pre-ceramic). Then, it was pre-sintered at 1050° C. for 2 h. Thereafter, the pre-sintered zirconia ceramics were taken out, equal amounts of color masking liquids from each group were painted on or over the surface of the zirconia ceramics respectively, which was repeated twice. Then, the zirconia ceramics were put into an oven for drying at 90° C., and half an hour later, taken out, put into a crucible with zirconium beads, put into a sintering furnace, and heated at 1530° C. for 2 hours to complete secondary sintering. At the same time, a control group was provided, where the pre-sintered zirconia ceramics were directly heated at 1530° C. for 2 h without prior painting with the color masking liquid.

TABLE 1

| Formula of mother liquor used in individual groups | | | | |
|---|---|---|---|---|
| Group | Ethylene glycol | Gluconic acid | Citric acid | Praseodymium nitrate |
| Group 1 | 18% | 3% | 2% | 2% |
| Group 2 | 20% | 3% | 2% | 2% |
| Group 3 | 23% | 3% | 2% | 2% |
| Group 4 | 20% | 1% | 2% | 2% |
| Group 5 | 20% | 5% | 2% | 2% |
| Group 6 | 20% | 3% | 1% | 2% |
| Group 7 | 20% | 3% | 3% | 2% |
| Group 8 | 20% | 3% | 2% | 1% |
| Group 9 | 20% | 3% | 2% | 3% |

2. Light transmittance test, three-point bending strength test, thickness test and color masking test were carried out for each group of zirconia bases. Among them, the thickness test is carried out as follows: the thickness of the zirconia bases in each group is measured at three points (the positions of the three points selected are the same for all the bases) respectively, and compared with that in the blank control group to obtain three groups of difference ratios which are then averaged. Thickness difference ratio lower than 1/10,000 is regarded as no difference. The color masking test comprises the following steps: the zirconia bases prepared in each group are fit onto the same metal abutments, and observed for whether the zirconia bases are transparent to color or not with naked eyes under a typical daily illumination condition, and observed for translucency and aesthetic quality. The results of these tests are shown in Table 2.

TABLE 2

Results for zirconium dioxide bases in individual groups

| Group | Light transmittance (%) | Bending strength (MPa) | Thickness difference | Transparent to color or not | Translucency |
|---|---|---|---|---|---|
| Group 1 | 21.2% | 1201 | No difference | No | Excellent |
| Group 2 | 15.3% | 1215 | No difference | No | Excellent |
| Group 3 | 19.2% | 1209 | No difference | No | Excellent |
| Group 4 | 19.6% | 1190 | No difference | No | Excellent |
| Group 5 | 21.5% | 1196 | No difference | No | Excellent |
| Group 6 | 25.2% | 1193 | No difference | No | Excellent |
| Group 7 | 20.5% | 1201 | No difference | No | Excellent |
| Group 8 | 26.4% | 1203 | No difference | No | Excellent |
| Group 9 | 31.5% | 1207 | No difference | No | Excellent |
| Control group | 42.1% | 1205 | N/A | Yes | Excellent |

3. A mother liquor was prepared with the formula of the mother liquor in group 2 in step 1, and then 14 groups of color masking liquids (group 10-group 23) were prepared with the mother liquor, wherein the formulas of these groups of color masking liquids are shown in Table 3, and the numerals in the following Table indicate the mass percentages of the corresponding components in the color masking liquid. The color masking liquid was used in the same way as above.

TABLE 3

Formula of color masking liquid used in color masking liquid in individual groups

| Group | Mother liquor | Alcohol | Amount | Potassium nitrate | Yttrium chloride | Citric acid |
|---|---|---|---|---|---|---|
| Group 10 | 95.00% | Ethanol | 4.15% | 0.30% | 0.20% | 0.35% |
| Group 11 | 96.63% | Ethanol | 2.52% | 0.30% | 0.20% | 0.35% |
| Group 12 | 96.83% | Ethanol | 1.52% | 0.30% | 0.20% | 0.35% |
| Group 13 | 97.88% | Ethanol | 1.27% | 0.30% | 0.20% | 0.35% |
| Group 14 | 95.00% | Ethanol | 1.52% | 2.93% | 0.20% | 0.35% |
| Group 15 | 96.63% | Ethanol | 1.52% | 1.30% | 0.20% | 0.35% |
| Group 16 | 96.83% | Ethanol | 1.52% | 1.10% | 0.20% | 0.35% |
| Group 17 | 97.88% | Ethanol | 1.52% | 0.05% | 0.20% | 0.35% |
| Group 18 | 96.93% | Ethanol | 1.52% | 1.10% | 0.10% | 0.35% |
| Group 19 | 96.93% | Ethanol | 1.52% | 1.10% | 0.30% | 0.35% |
| Group 20 | 96.93% | Ethanol | 1.52% | 1.10% | 0.20% | 0.20% |
| Group 21 | 96.93% | Ethanol | 1.52% | 1.10% | 0.20% | 0.40% |
| Group 22 | 96.83% | Ethylene glycol | 1.52% | 1.10% | 0.20% | 0.35% |
| Group 23 | 96.83% | Methanol | 1.52% | 1.10% | 0.20% | 0.35% |

4. Light transmittance test, three-point bending strength test, thickness test and color masking test were carried out on each group of zirconia bases. Among them, the thickness test is carried out as follows: the thickness of the zirconia bases in each group is measured at three points (the positions of the three points selected are the same for all the bases) respectively, and compared with that in the blank control group to obtain three groups of difference ratios which are then averaged. The color masking test comprises the following steps: the zirconia bases prepared in each group are fit onto the same metal abutments, and observed for whether the zirconia bases are transparent to color or not with naked eyes under a typical daily illumination condition. The results of these tests are shown in Table 4.

TABLE 4

Results for zirconium dioxide bases in individual groups

| Group | Light transmittance (%) | Bending strength (MPa) | Thickness difference | Transparent to color or not | Translucency |
|---|---|---|---|---|---|
| Group 10 | 26.5% | 1209 | No difference | No | Excellent |
| Group 11 | 23.2% | 1210 | No difference | No | Excellent |
| Group 12 | 28.4% | 1210 | No difference | No | Excellent |
| Group 13 | 31.2% | 1213 | No difference | No | Excellent |
| Group 14 | 17.2% | 1198 | No difference | No | Excellent |
| Group 15 | 16.3% | 1203 | No difference | No | Excellent |
| Group 16 | 15.2% | 1217 | No difference | No | Excellent |
| Group 17 | 33.6% | 1209 | No difference | No | Excellent |
| Group 18 | 19.2% | 1213 | No difference | No | Excellent |
| Group 19 | 20.0% | 1213 | No difference | No | Excellent |
| Group 20 | 16.3% | 1208 | No difference | No | Excellent |
| Group 21 | 17.6% | 1206 | No difference | No | Excellent |
| Group 22 | 16.1% | 1213 | No difference | No | Excellent |
| Group 23 | 15.9% | 1211 | No difference | No | Excellent |

Example 2: Effect of Methods for Applying Color Masking Liquids

1. Eight groups of color masking liquids were prepared using the formula of group 16 in Example 1, and then applied by different methods. Specifically, the treatment methods for these groups are shown in Table 5.

TABLE 5

Comparison of methods for applying color masking liquids in individual groups

| Group | Stage in Method at which zirconia bases are painted with color masking liquid | No. of times that zirconia bases are painted with color masking liquid | Dried or not? | Drying temperature |
|---|---|---|---|---|
| Group 1 | Before secondary sintering of zirconia base | 2 | Yes | 90° C. |
| Group 2 | After secondary sintering of zirconia base | 2 | Yes | 90° C. |
| Group 3 | Before secondary sintering of zirconia base | 1 | Yes | 90° C. |
| Group 4 | Before secondary sintering of zirconia base | 4 | Yes | 90° C. |
| Group 5 | Before secondary sintering of zirconia base | 2 | No | N/A |
| Group 6 | Before secondary sintering of zirconia base | 2 | Yes | 30° C. |
| Group 7 | Before secondary sintering of zirconia base | 2 | Yes | 60° C. |
| Group 8 | Before secondary sintering of zirconia base | 2 | Yes | 120° C. |

2. A group of zirconia bases were prepared separately without painting with the masking liquid, and other preparation and sintering conditions were completely the same, which served as the blank control group. The results of these groups are shown in Table 6. Among them, "not dried" means the bases are directly sintered without drying.

TABLE 6

Results for zirconia bases in all groups

| Group | Light transmittance (%) | Bending strength (MPa) | Thickness difference | Transparent to color or not? | Translucency |
|---|---|---|---|---|---|
| Group 1 | 15.6% | 1213 | No difference | No | Excellent |
| Group 2 | 33.7% | 1203 | +3‰ | No | Good |
| Group 3 | 29.3% | 1207 | No difference | Yes | Excellent |
| Group 4 | 10.5% | 1210 | No difference | No | Good |
| Group 5 | 28.6% | 1198 | No difference | No | Good |
| Group 6 | 23.6% | 1203 | No difference | No | Excellent |
| Group 7 | 21.3% | 1205 | No difference | No | Excellent |
| Group 8 | 19.1% | 1210 | No difference | No | Excellent |
| Blank control group | 43.2% | 1207 | / | Yes | Excellent |

Zirconia bases were obtained with the formula of group 16 in Example 1 using the method of group 1 in Example 2. Then, the zirconia base was colored. Of course, the zirconia base can be colored directly without being treated with the color masking liquid. In the latter case, the translucency and color masking property of the zirconia base may be inferior.

The present disclosure provides the following two coloring methods. Method 1 involves preparing a first coloring liquid, roughening the surface of the zirconia base, soaking the zirconia base in the first coloring liquid for more than 15 s, then taking out the zirconia base, and subjecting the zirconia base to surface protection treatment using the adhesive solution. The advantage of Method 1 is that the coloring speed is fast, and the coloring depth does not change after a certain time (15 s), which is convenient for dentists to operate.

Method 2 involves preparing a second coloring liquid, preparing an adhesive solution, mixing the second coloring liquid and the adhesive solution, painting the mixed solution on or over the surface of the zirconia base, or soaking the zirconia base in the mixed solution, then crystallizing at a high temperature, and finally painting a layer of silane coupling agent on or over the surface of the zirconia base for protection. The advantage of Method 2 is that the coloring process is simple, and a protective film will be formed on or over the surface of the zirconia base after coloring, thus prolonging the service life of the base.

Method 1 and Method 2 are described in detail below.

Method 1:

1. The first coloring liquid comprises a first coloring agent, a first dispersant and a first solvent which are, in mass percentages, 0.01-26%, 0.2-35% and 60-97% of the first coloring liquid respectively.

The first coloring agent is at least one of erbium chloride, ferric chloride and manganese nitrate. Preferably, the coloring agent includes each of erbium chloride, ferric chloride and manganese nitrate in mass percentages of 0.5-13% of erbium chloride, 0.5-6% of ferric chloride, and 0.01-6% of manganese nitrate by weight of the coloring liquid. The first dispersant is polyethylene glycol; and the first solvent is deionized water.

The method for preparing the first coloring liquid comprises the following steps: weighing raw materials according to the above-mentioned mass percentages, adding erbium chloride, ferric chloride, manganese nitrate and polyethylene glycol into the deionized water, stirring them uniformly, and sub-packaging the mixture for later use.

2. The method for coloring the zirconia base specifically comprises the following steps.
   (1) Surface roughening treatment is carried out on the zirconia base. Specifically, surface sandblasting treatment and hot acid treatment are carried out on the zirconia denture to control the surface roughness of the zirconia denture.
   The sandblasting treatment involves sandblasting the zirconia denture with 30-60 μm zirconia powder under a pressure of 0.2-0.3 MPa for 5-10 s. The hot acid treatment involves mixing hydrochloric acid and nitric acid thoroughly, heating them to 70-80° C. to obtain a mixed acid solution, and soaking the zirconia denture with sandblasted surface in 15-30 ml of the mixed acid solution (e.g., at 70-80° C.) for 10-15 min. The concentration of hydrochloric acid is 1-2 mol/L, the concentration of nitric acid is 1-2 mol/L, and the volume ratio of hydrochloric acid to nitric acid is 1:2-3.
   (2) The roughened zirconia base is washed 3-5 times with deionized water, and then the zirconia base is soaked with the first coloring liquid for more than 15 s. After 15 s, the color of the colored zirconia base will not deepen with prolonged soaking times (i.e., soaking times longer than 15 seconds).
   (3) The colored zirconia base is put into a denture sintering furnace, where the base is heated to 1530° C. at a rate of 5° C./min, kept at this temperature for crystallization for 120 min, and then allowed to cool down along with the furnace.
   (4) Preferably, after step (2) is finished, the zirconia base is soaked in a silane coupling agent for 1-2 min, and then soaked in a resin binder for 3-10 min. After soaking, the zirconia base is put in an oven at 90-150° C. for drying for 30 min, and then put in a denture sintering furnace where the base is heated to 1530° C. at a rate of 5° C./min, kept at this temperature for crystallization for 120 min, and then allowed to cool down along with the furnace.

Method 1 will be further explained with specific examples below.

Example 3: Demonstration of Effect of Roughening Treatment in Method 1

According to the above method, zirconia dentures were subjected to surface roughening treatment. A total of 18 groups were set, with their specific parameters as shown in Table 7 below. Specifically, the zirconia dentures after surface sandblasting were soaked in 20 mL of the mixed acid solution at a temperature of 80° C. Those receiving no treatment were used as the control.

TABLE 7

Surface roughening treatment of zirconia denture

| | Surface sandblasting treatment | | | Hot acid treatment | | | |
|---|---|---|---|---|---|---|---|
| Group | Particle size (μm) | Pressure (MPa) | Processing time (s) | Hydrochloric acid concentration (mol · L$^{-1}$) | Nitric acid concentration (mol · L$^{-1}$) | Volume ratio of HCl to nitric acid | Soaking time (min) |
| Group 1 | 30 | 0.2 | 5 | 1 | 1 | 1:2 | 10 |
| Group 2 | 30 | 0.2 | 7 | 1 | 1 | 1:2 | 12.5 |
| Group 3 | 30 | 0.2 | 10 | 1 | 1 | 1:2 | 15 |
| Group 4 | 30 | 0.3 | 5 | 1 | 1 | 1:3 | 10 |
| Group 5 | 30 | 0.3 | 7 | 1 | 1 | 1:3 | 12.5 |
| Group 6 | 30 | 0.3 | 10 | 1 | 1 | 1:3 | 15 |
| Group 7 | 45 | 0.2 | 5 | 1 | 2 | 1:2 | 10 |
| Group 8 | 45 | 0.2 | 7 | 1 | 2 | 1:2 | 12.5 |
| Group 9 | 45 | 0.2 | 10 | 1 | 2 | 1:2 | 15 |
| Group 10 | 45 | 0.3 | 5 | 1 | 2 | 1:3 | 10 |
| Group 11 | 45 | 0.3 | 7 | 1 | 2 | 1:3 | 12.5 |
| Group 12 | 45 | 0.3 | 10 | 1 | 2 | 1:3 | 15 |
| Group 13 | 60 | 0.2 | 5 | 2 | 1 | 1:2 | 10 |
| Group 14 | 60 | 0.2 | 7 | 2 | 1 | 1:2 | 12.5 |
| Group 15 | 60 | 0.2 | 10 | 2 | 1 | 1:2 | 15 |
| Group 16 | 60 | 0.3 | 5 | 2 | 1 | 1:3 | 10 |
| Group 17 | 60 | 0.3 | 7 | 2 | 1 | 1:3 | 12.5 |
| Group 18 | 60 | 0.3 | 10 | 2 | 1 | 1:3 | 15 |

The treated zirconia dentures in the individual groups were soaked in water for 2-5 min, and then air-dried for later use.

Example 4: Demonstration of Effect of Coloring Liquid in Method 1

Coloring liquids were prepared, with the formula of raw materials including erbium chloride, ferric chloride, manganese nitrate, polyethylene glycol and deionized water in ratios as shown in Table 8 below. The results showed that there was no obvious change in the color of the three coloring liquids prepared in each group. The color of groups a-c gradually deepened from orange, the color of groups d-f gradually deepened from yellow, the color of groups g-i gradually deepened from gray red, and the color of groups j-l gradually deepened from yellow red.

TABLE 8

Formula of coloring liquid

Mass ratio of raw materials, %

| Group | Erbium chloride Concentration (mmol·L⁻¹) | Amount | Ferric chloride Concentration (mmol·L⁻¹) | Amount | Manganese nitrate Concentration (mmol·L⁻¹) | Amount | Polyethylene glycol | Deionized water |
|---|---|---|---|---|---|---|---|---|
| Group a | 5.4 | 3 | 5.7 | 1.2 | 5.3 | 0.5 | 2 | 93.3 |
|  | 5.4 | 3 | 5.7 | 1.2 | 5.3 | 0.5 | 6 | 89.3 |
|  | 5.4 | 3 | 5.7 | 1.2 | 5.3 | 0.5 | 10 | 85.3 |
| Group b | 6.1 | 3 | 6.4 | 1.2 | 6.6 | 0.5 | 2 | 93.3 |
|  | 6.1 | 3 | 6.4 | 1.2 | 6.6 | 0.5 | 6 | 89.3 |
|  | 6.1 | 3 | 6.4 | 1.2 | 6.6 | 0.5 | 10 | 85.3 |
| Group c | 7.5 | 3 | 7.2 | 1.2 | 7.7 | 0.5 | 2 | 93.3 |
|  | 7.5 | 3 | 7.2 | 1.2 | 7.7 | 0.5 | 6 | 89.3 |
|  | 7.5 | 3 | 7.2 | 1.2 | 7.7 | 0.5 | 10 | 85.3 |
| Group d | 5.4 | 1.2 | 5.7 | 1.5 | 5.3 | 0.3 | 2 | 95.0 |
|  | 5.4 | 1.2 | 5.7 | 1.5 | 5.3 | 0.3 | 6 | 91.0 |
|  | 5.4 | 1.2 | 5.7 | 1.5 | 5.3 | 0.3 | 10 | 87.0 |
| Group e | 6.1 | 1.2 | 6.4 | 1.5 | 6.6 | 0.3 | 2 | 95.0 |
|  | 6.1 | 1.2 | 6.4 | 1.5 | 6.6 | 0.3 | 6 | 91.0 |
|  | 6.1 | 1.2 | 6.4 | 1.5 | 6.6 | 0.3 | 10 | 87.0 |
| Group f | 7.5 | 1.2 | 7.2 | 1.5 | 7.7 | 0.3 | 2 | 95.0 |
|  | 7.5 | 1.2 | 7.2 | 1.5 | 7.7 | 0.3 | 6 | 91.0 |
|  | 7.5 | 1.2 | 7.2 | 1.5 | 7.7 | 0.3 | 10 | 87.0 |
| Group g | 5.4 | 1.1 | 5.7 | 0.8 | 5.3 | 0.7 | 2 | 95.4 |
|  | 5.4 | 1.1 | 5.7 | 0.8 | 5.3 | 0.7 | 6 | 91.4 |
|  | 5.4 | 1.1 | 5.7 | 0.8 | 5.3 | 0.7 | 10 | 87.4 |
| Group h | 6.1 | 1.1 | 6.4 | 0.8 | 6.6 | 0.7 | 2 | 95.4 |
|  | 6.1 | 1.1 | 6.4 | 0.8 | 6.6 | 0.7 | 6 | 91.4 |
|  | 6.1 | 1.1 | 6.4 | 0.8 | 6.6 | 0.7 | 10 | 87.4 |
| Group I | 7.5 | 1.1 | 7.2 | 0.8 | 7.7 | 0.7 | 2 | 95.4 |
|  | 7.5 | 1.1 | 7.2 | 0.8 | 7.7 | 0.7 | 6 | 91.4 |
|  | 7.5 | 1.1 | 7.2 | 0.8 | 7.7 | 0.7 | 10 | 87.4 |
| Group j | 5.4 | 0.8 | 5.7 | 0.9 | 5.3 | 0.9 | 2 | 95.4 |
|  | 5.4 | 0.8 | 5.7 | 0.9 | 5.3 | 0.9 | 6 | 91.4 |
|  | 5.4 | 0.8 | 5.7 | 0.9 | 5.3 | 0.9 | 10 | 87.4 |
| Group k | 6.1 | 0.8 | 6.4 | 0.9 | 6.6 | 0.9 | 2 | 95.4 |
|  | 6.1 | 0.8 | 6.4 | 0.9 | 6.6 | 0.9 | 6 | 91.4 |
|  | 6.1 | 0.8 | 6.4 | 0.9 | 6.6 | 0.9 | 10 | 87.4 |
| Group l | 7.5 | 0.8 | 7.2 | 0.9 | 7.7 | 0.9 | 2 | 95.4 |
|  | 7.5 | 0.8 | 7.2 | 0.9 | 7.7 | 0.9 | 6 | 91.4 |
|  | 7.5 | 0.8 | 7.2 | 0.9 | 7.7 | 0.9 | 10 | 87.4 |

Example 5: Demonstration of Effect of Coloring Time in Method 1

The coloring liquid with an orange color and a polyethylene glycol content of 6% in group a in Table 8 was selected to color the treated zirconia dentures in Table 1, with the coloring time and color change of zirconia dentures shown in Table 9 below. In particular, coloring time refers to the time when the color of zirconia denture no longer changes. The results showed that after the zirconia denture was treated according to the parameters in group 7, the time for the zirconia denture to reach the specified color and balance became shorter.

TABLE 9

Coloring time and color change of zirconia denture in individual groups

| Group | Coloring time (s) | Color change |
|---|---|---|
| Group 1 | 30 | The color was lighter than the specified color |
| Group 2 | 38 | The color was lighter than the specified color |
| Group 3 | 45 | The color was lighter than the specified color |
| Group 4 | 50 | The specified color was reached at 20 s, and with the extension of coloring time, the color gradually deepened, and the color did not change any more after 50 s |
| Group 5 | 60 | The specified color was reached at 22 s, and with the extension of coloring time, the color gradually deepened, and did not change any more after 60 s |
| Group 6 | 68 | The specified color was reached at 25 s, and with the extension of coloring time, the color gradually deepened, and after 68 s, reached equilibrium and did not change any more |

TABLE 9-continued

Coloring time and color change of zirconia denture in individual groups

| Group | Coloring time (s) | Color change |
|---|---|---|
| Group 7 | 35 | The specified color was reached at 15 s, and with the extension of coloring time, the color gradually deepened, and after 35 s, reached equilibrium and did not change any more |
| Group 8 | 42 | The specified color was reached at 17 s, and with the extension of coloring time, the color gradually deepened, and after 42 s, reached equilibrium and did not change any more |
| Group 9 | 48 | The specified color was reached at 20 s, and with the extension of coloring time, the color gradually deepened, and after 48 s, reached equilibrium and did not change any more |
| Group 10 | 45 | The specified color was reached at 23 s, and with the extension of coloring time, the color gradually deepened, and after 45 s, reached equilibrium and did not change any more |
| Group 11 | 52 | The specified color was reached at 27 s, and with the extension of coloring time, the color gradually deepened, and after 52 s, reached equilibrium and did not change any more |
| Group 12 | 61 | The specified color was reached at 30 s, and with the extension of coloring time, the color gradually deepened, and after 61 s, reached equilibrium and did not change any more |
| Group 13 | 58 | The specified color was reached at 26 s, and with the extension of coloring time, the color gradually deepened, and after 58 s, reached equilibrium and did not change any more |
| Group 14 | 70 | The specified color was reached at 30 s, and with the extension of coloring time, the color gradually deepened, and after 70 s, reached equilibrium and did not change any more |
| Group 15 | 81 | The specified color was reached at 35 s, and with the extension of coloring time, the color gradually deepened, and after 81 s, reached equilibrium and did not change any more |
| Group 16 | 64 | The specified color was reached at 40 s, and with the extension of coloring time, the color gradually deepened, and after 64 s, reached equilibrium and did not change any more |
| Group 17 | 75 | The specified color was reached at 45 s, and with the extension of coloring time, the color gradually deepened, and after 75 s, reached equilibrium and did not change any more |
| Group 18 | 83 | The specified color was reached at 52 s, and with the extension of coloring time, the color gradually deepened, and after 83 s, reached equilibrium and did not change any more |
| Control group | 120 | The specified color was reached at 60 s, and with the extension of coloring time, the color gradually deepened, and after 120 s, reached equilibrium and did not change any more |

Example 6: Demonstration of Effect of Polyethylene Glycol in Method 1

After the zirconia denture was treated according to the parameters in group 7, the effect of polyethylene glycol content on coloring time was investigated, as shown in Table 10 below. The results showed that when the content of polyethylene glycol was 10%, the color of the denture remained unchanged with the extension of soaking time after 15 s.

TABLE 10

Effect of polyethylene glycol content on soaking time

| Group | Mass ratio of raw materials, % | | | | | Soaking time of denture/s | | | | | | |
|---|---|---|---|---|---|---|---|---|---|---|---|---|
| | Erbium chloride | Ferric chloride | Manganese nitrate | Polyethylene glycol | Deionized water | 5 | 10 | 15 | 30 | 120 | 240 | 600 |
| Group 1 | 3 | 1.2 | 0.5 | 2 | 93.3 | Lighter | Lighter | Normal | Slightly darker | Darker | Darker | Darker |
| Group 2 | 3 | 1.2 | 0.5 | 6 | 89.3 | Lighter | Lighter | Normal | Slightly darker | Darker | Darker | Darker |
| Group 3 | 3 | 1.2 | 0.5 | 10 | 85.3 | Lighter | Lighter | Normal | Normal | Normal | Normal | Normal |
| Group 4 | 3 | 1.2 | 0.5 | 20 | 75.3 | Lighter | Lighter | Normal | Normal | Normal | Normal | Normal |
| Group 5 | 4 | 0.8 | 0.3 | 10 | 84.9 | Lighter | Lighter | Normal | Normal | Normal | Normal | Normal |
| Group 6 | 5 | 0.6 | 0.2 | 10 | 84.2 | Lighter | Lighter | Normal | Normal | Normal | Normal | Normal |
| Group 7 | 6 | 0.4 | 0.2 | 10 | 83.4 | Lighter | Lighter | Normal | Normal | Normal | Normal | Normal |

Example 7: Protection Treatment in Method 1

The dentures colored in group 3 in Example 6 were soaked in the silane coupling agent for 1-2 min, and then soaked in the resin binder for 3-10 min, so that the resin binder infiltrated into micro-pores on the surface of zirconia dentures to seal the coloring liquid soaked into the pores and form a transparent film on or over the surface of zirconia dentures, which effectively avoided the fading of dentures and the penetration of bacteria, acids, enzymes and products thereof in human oral cavities into the pores on the surface of zirconia dentures. After soaking, the zirconia dentures were dried in an oven at 90-150° C. for 30 min, then put into a denture sintering furnace, heated to 1530° C. at a rate of 5° C./min, kept at this temperature to crystallize for 120 min, and then cooled down along with the furnace.

Specifically, the resin binder contains 10-methacryloxy-decyl phosphate (MDP) monomer, and the resin binder and silane coupling agent are common dental reagents.

Method 2:

1. The second coloring liquid comprises a second coloring agent, a second dispersant, a complexing agent and a second solvent in mass percentages of 0.01-48%, 0.1-5%, 0.05-2%, and 45-99% of the coloring liquid, respectively.

Specifically, the second coloring agent is one or a mixture of two or more of erbium chloride, ferric chloride, neodymium nitrate, manganese nitrate, ammonium metavanadate, cerium nitrate, praseodymium nitrate, cobalt nitrate and nickel nitrate. The second dispersant is polyethylene glycol, polyacrylic acid or polyurethane. The complexing agent is citric acid, glucose, ethylenediaminetetraacetic acid, sodium citrate or 2,3-dimercaptosuccinic acid. The second solvent is deionized water. Different coloring agents can be mixed to obtain coloring liquids with different colors which can be any one of blue, gray, tetracycline yellow, tetracycline gray, tetracycline brown, brown, pink, red, purple, green or black.

The coloring liquid is prepared by adding all the components into the solvent and mixing them well.

2. The adhesive solution consists of 40-100 parts of a matrix, 2-6 parts of a diluent, 3-5 parts of an adhesive monomer, 6-15 parts of a polymerization inhibitor, 30-55 parts of carbon nanotubes, 20-60 parts of a filler, 1-8 parts of tartaric acid and 30-70 parts of water.

The matrix consists of bisphenol A-glycidyl methacrylate (Bis-GMA), an epoxy resin and 10-methacryloxydecyl phosphate (MDP); or bisphenol-s-bis(3-methacryloyloxy-2-hydroxypropyl)ether, epoxy resin and 10-methacryloyloxy-decyl phosphate. Preferably, the matrix is a mixture of bisphenol A-glycidyl methacrylate, the epoxy resin and 10-methacryloxydecyl phosphate in a mass ratio of 1:1:1-3.

The diluent is a methacrylate, the adhesive monomer is 4-methacryloyloxyethyl trimellitic anhydride (4-META), and the polymerization inhibitor is one or a mixture of two or more of tert-butyl hydroquinone (TBHQ), hydroquinone (HQ) and p-tert-butyl catechol (TBC). Preferably, the polymerization inhibitor is a mixture of tert-butyl hydroquinone, hydroquinone and p-tert-butyl catechol in a mass ratio of 1:1:1.

The filler is obtained by pretreating various metal oxides. The metal oxides are a mixture of two or more of silicon dioxide, aluminum oxide, calcium fluoride and titanium dioxide, and preferably, a mixture of silicon dioxide, aluminum oxide and calcium fluoride in a mass ratio of 1:1:1. The specific pretreatment process comprises melting the metal oxides, uniformly mixing them, and then subjecting them to quenching and grinding. In one example, the metal oxides may be melted in sequence, according to their melting points, from high to low. The particle size of the filler after grinding is smaller than the diameter of the carbon nanotube.

The adhesive solution is prepared as follows:
(1) Bisphenol A-glycidyl methacrylate, epoxy resin and 10-methacryloyloxydecyl phosphate in the specified ratio are added into water, mixed uniformly, then the methacrylate and 4-methacryloyloxy ethyl trimellitic anhydride are added, and the mixture is stirred uniformly for later use.
(2) Silicon dioxide, aluminum oxide and calcium fluoride are melted in sequence according to their respective melting points, from high to low. Specifically, aluminum oxide is melted firstly, then silicon dioxide and finally calcium fluoride. The melted compounds are kept at the melting point of calcium fluoride for 15-30 min to achieve phase balance. Thereafter, the melted compounds are put into water for quenching, so that the melted compounds are solidified into a solid mixture, and when the temperature of the solid mixture is 200-300° C., the solid mixture is put into an oil and cooled to room temperature. The solid mixture is taken out and dried, and then crushed until the particle size is smaller than the diameter of the carbon nanotubes. In some cases, the particle size of the filler changes with the diameter of the carbon nanotubes used, and the particle size of the filler is always kept smaller than the diameter of the carbon nanotubes, preferably smaller than $\frac{1}{4}$-$\frac{1}{2}$ of the diameter of the carbon nanotubes, thereby obtaining a filler powder.
(3) The filler powder obtained in step (2) is added into the mixed liquid obtained in step (1), and then ultrasonic dispersion is carried out, wherein the vibration frequency is 12-16 kHz, and the dispersion time is 10-20 min. Then, a mixture of tert-butyl hydroquinone, hydroquinone and p-tert-butyl catechol is added thereto, and stirred uniformly to obtain a mixed solution. Finally, carbon nanotubes with a diameter of 10-20 nm and a length of 0.5-2 μm are added into the mixed solution, and ultrasonic dispersion is continued for 15-30 min with a vibration frequency of 19-25 kHz.
(4) Tartaric acid (TA) is added to the solution obtained in step (3), so as to adjust the solidification time of the whole reaction system and improve its operability, and an adhesive solution is obtained after stirring uniformly. Meanwhile, according to the situation, an appropriate amount of water can be added to the adhesive solution to adjust the consistency and/or viscosity of the adhesive solution.

3. The coloring treatment method of the zirconia base is specifically as follows.
(1) The zirconia base is roughened according to the surface roughening treatment method in Method 1, and then washed. If necessary, a neutralization reaction is carried out before washing.
(2) The second coloring liquid is added into the adhesive solution. The amount of the adhesive solution is conventionally selected according to the actual condition of the zirconia denture to be colored, and the color depth of the coloring liquid is adjusted by controlling the concentration of metal ions in the coloring liquid, so as to control the color finally displayed after the coloring liquid is mixed with the adhesive solution. Finally, the zirconia denture is colored to be consistent with the color of the patient's teeth. Specifically, the volume ratio of adhesive solution to the second coloring liquid is 1-3:1. According to this ratio, the color of the mixed solution is adjusted to make the color of the mixed solution consistent with the color of the patient's teeth, so that the color of the colored zirconia denture is consistent with the color of the patient's teeth.

Specifically, the coloring process is carried out as follows. According to the color of the patient's teeth, a small amount of the coloring liquid with the adhesive solution is taken by dipping with a 2 mm coloring pen to paint the surface of the denture surface, with the painting amount controlled according to the color depth of the patient's teeth. After painting, the denture is put into an oven at 90-150° C. for drying for 30 min, then taken out and put into a denture sintering furnace to heat up to 1530° C. at a rate of 5° C./min, kept at this temperature for crystallization for 120 min, and then cooled down along with the furnace. Alternatively, the zirconia denture can be put into the coloring liquid with the adhesive solution, and after the color of the zirconia denture is observed to be consistent with that of the patient's teeth, the zirconia denture can be taken out, and then the subsequent sintering operation can be carried out.

Further preferably, in order to make the bonding between the coloring liquid containing the adhesive solution and the zirconia denture firmer, a layer of silane coupling agent can be painted on or over the surface of zirconia denture, so as to improve the bonding strength between the coloring liquid containing the adhesive solution and the zirconia denture.

Method 2 will be further explained with specific examples below.

Example 8: The Second Coloring Liquid with Different Colors in Method 2

1. Blue second coloring liquids were prepared using raw materials including neodymium nitride, polyethylene glycol, citric acid and deionized water. The specific raw material composition and displayed color of the coloring liquids are shown in Table 11 below.

TABLE 11

| Composition and displayed color of blue coloring liquids | | | | | |
|---|---|---|---|---|---|
| Mass ratio of raw materials, % | | | | | |
| Neodymium nitride | | | | | |
| Concentration mmol·$L^{-1}$ | Amount | Polyethylene glycol | Citric acid | Deionized water | Color |
| 6.2 | 1 | 1 | 0.2 | 97.8 | The color gradually deepened from light blue to blue, and finally showed normal blue |
| 7.6 | 2 | 1 | 0.2 | 96.8 | |
| 8.7 | 3 | 1 | 0.2 | 95.8 | |

2. Second coloring liquids with gray color were prepared using raw materials including manganese nitrate, polyethylene glycol, citric acid and deionized water. The specific raw material composition and displayed color of the coloring liquids are shown in Table 12 below.

TABLE 12

| Composition and displayed color of blue coloring liquids | | | | | |
|---|---|---|---|---|---|
| Mass ratio of raw materials, % | | | | | |
| Manganese nitrate | | | | | |
| Concentration (mmol·$L^{-1}$) | Amount | Polyethylene glycol | Citric acid | Deionized water | Color |
| 4.9 | 0.05 | 1 | 0.2 | 98.75 | The color gradually deepened from light gray to gray, and finally showed normal gray |
| 6.1 | 0.10 | 1 | 0.2 | 98.70 | |
| 9.1 | 0.15 | 1 | 0.2 | 98.65 | |

3. Coloring liquids with tetracycline yellow color were prepared using raw materials including erbium chloride, manganese nitrate, ammonium metavanadate, cerium nitrate, polyethylene glycol, citric acid and deionized water. The specific raw material composition and displayed color of the coloring liquids are shown in Table 13 below.

TABLE 13

| Composition and displayed color of tetracycline yellow coloring liquids | | | | | | | | | | |
|---|---|---|---|---|---|---|---|---|---|---|
| Mass ratio of raw materials, % | | | | | | | | | | |
| Erbium chloride | | Manganese nitrate | | Ammonium vanadate | | Cerium nitrate | | | | |
| Concentration | Amt. | Concentration | Amt. | Concentration | Amt. | Concentration | Amt. | Polyethylene glycol | Citric acid | Deionized water | Color |
| 5.6 | 2.833 | 3.5 | 0.266 | 4.3 | 0.005 | 4.1 | 2.86 | 1 | 0.2 | 92.836 | The color gradually deepened from light to dark, and finally showed normal tetracycline yellow |
| 6.8 | 4.25 | 4.7 | 0.4 | 6.5 | 0.075 | 5.7 | 2.86 | 1 | 0.2 | 91.215 | |
| 8.4 | 8.5 | 6.2 | 0.8 | 8.1 | 0.015 | 7.6 | 2.86 | 1 | 0.2 | 86.625 | |

Note:
Concentration is in mmol/l in Table 13.

4. Coloring liquids with tetracycline gray color were prepared using raw materials including erbium chloride, ferric chloride, manganese nitrate, polyethylene glycol, citric acid and deionized water. The specific raw material composition and displayed color of the coloring liquids are shown in Table 14 below.

TABLE 14

Composition and displayed color of tetracycline grey coloring liquids

| Mass ratio of raw materials, % | | | | | | | | |
|---|---|---|---|---|---|---|---|---|
| Erbium chloride | | Ferric chloride | | Manganese nitrate | | Polyethylene glycol | Citric acid | Deionized water | Color |
| Concentration | Amt. | Concentration | Amt. | Concentration | Amt. | | | | |
| 6.5 | 2 | 4.5 | 0.466 | 5.6 | 0.733 | 1 | 0.2 | 95.601 | The color gradually deepened from light to dark, and finally showed normal tetracycline gray |
| 8.2 | 3 | 6.2 | 0.7 | 7.1 | 1.1 | 1 | 0.2 | 94.0 | |
| 10.3 | 6 | 7.2 | 1.4 | 8.8 | 2.2 | 1 | 0.2 | 89.2 | |

Note: Concentration is in mmol/l in Table 14.

5. Coloring liquids with tetracycline brown color were prepared using raw materials including erbium chloride, ferric chloride, polyethylene glycol, citric acid and deionized water. The specific raw material composition and displayed color of the coloring liquids are shown in Table 15 below.

TABLE 15

Composition and displayed color of tetracycline brown coloring liquids

| Mass ratio of raw materials, % | | | | | | | |
|---|---|---|---|---|---|---|---|
| Erbium chloride | | Ferric chloride | | Polyethylene glycol | Citric acid | Deionized water | Color |
| Concentration (mmol · L$^{-1}$) | Amount | Concentration (mmol · L$^{-1}$) | Amount | | | | |
| 4.1 | 2.333 | 6.9 | 0.733 | 1 | 0.2 | 95.734 | The color gradually deepened from light to dark, and finally showed normal tetracycline brown |
| 5.2 | 3.5 | 8.8 | 1.1 | 1 | 0.2 | 94.2 | |
| 6.4 | 7 | 10.5 | 2.2 | 1 | 0.2 | 89.6 | |

6. Brown coloring liquids were prepared using raw materials including erbium chloride, ferric chloride, praseodymium nitrate, cobalt nitrate, polyethylene glycol, citric acid and deionized water. The specific raw material composition and displayed color of the coloring liquids are shown in Table 16 below.

TABLE 16

Composition and displayed color of brown coloring liquids

| Mass ratio of raw materials, % | | | | | | | | | | | |
|---|---|---|---|---|---|---|---|---|---|---|---|
| Erbium chloride | | Ferric chloride | | Praseodymium nitrate | | Cobalt nitrate | | Polyethylene glycol | Citric acid | Deionized water | Color |
| Concentration | Amt. | Concentration | Amt. | Concentration | Amt. | Concentration | Amt. | | | | |
| 2.6 | 2.266 | 2.8 | 0.733 | 3.1 | 0.016 | 3.2 | 0.05 | 1 | 0.2 | 95.735 | The color gradually deepened from light to dark, and finally showed normal brown |
| 4.1 | 2.3 | 4.2 | 1.1 | 4.3 | 0.025 | 5.3 | 0.075 | 1 | 0.2 | 95.3 | |
| 5.3 | 6.8 | 5.1 | 2.2 | 5.1 | 0.05 | 7.1 | 0.15 | 1 | 0.2 | 89.6 | |

Note: Concentration is in mmol/l in Table 16.

7. Coloring liquids with pink color were prepared using raw materials including erbium chloride, polyethylene glycol, citric acid and deionized water. The specific raw material composition and displayed color of the coloring liquids are shown in Table 17 below.

TABLE 17

Composition and displayed color of pink coloring liquids

Mass ratio of raw materials, %

Erbium chloride

| Concentration (mmol·L$^{-1}$) | Amount | Polyethylene glycol | Citric acid | Deionized water | Color |
|---|---|---|---|---|---|
| 7.8 | 5 | 1 | 0.2 | 93.8 | The color |
| 12.5 | 10 | 1 | 0.2 | 88.8 | gradually |
| 16.3 | 20 | 1 | 0.2 | 78.8 | deepened from light pink to pink, and finally showed normal pink |

8. Coloring liquids with red color were prepared using raw materials including erbium chloride, polyethylene glycol, citric acid and deionized water. The specific raw material composition and displayed color of the coloring liquids are shown in Table 18 below.

TABLE 18

Composition and displayed color of red coloring liquids

Mass ratio of raw materials, %

Erbium chloride

| Concentration (mmol·L$^{-1}$) | Amount | Polyethylene glycol | Citric acid | Deionized water | Color |
|---|---|---|---|---|---|
| 25.6 | 10 | 1 | 0.2 | 88.8 | The color |
| 31.2 | 20 | 1 | 0.2 | 78.8 | gradually |
| 36.4 | 40 | 1 | 0.2 | 58.8 | deepened from light red to red, and finally showed normal red |

9. Coloring liquids with purple color were prepared using raw materials including neodymium nitrate, polyethylene glycol, citric acid and deionized water. The specific raw material composition and displayed color of the coloring liquids are shown in Table 19 below.

TABLE 19

Composition and displayed color of purple coloring liquids

Mass ratio of raw materials, %

Neodymium nitride

| Concentration (mmol·L$^{-1}$) | Amount | Polyethylene glycol | Citric acid | Deionized water | Color |
|---|---|---|---|---|---|
| 38.8 | 1 | 1 | 0.2 | 95.8 | The color |
| 45.2 | 4 | 1 | 0.2 | 94.8 | gradually |
| 54.6 | 6 | 1 | 0.2 | 92.8 | deepened from light purple to purple, and finally showed normal purple |

10. Coloring liquids with green color were prepared using raw materials including nickel nitrate, polyethylene glycol, citric acid and deionized water. The specific raw material composition and displayed color of the coloring liquids are shown in Table 20 below.

TABLE 20

Composition and displayed color of green coloring liquids

Mass ratio of raw materials, %

Nickel nitrate

| Concentration (mmol·L$^{-1}$) | Amount | Polyethylene glycol | Citric acid | Deionized water | Color |
|---|---|---|---|---|---|
| 8.9 | 0.01 | 1 | 0.2 | 98.79 | The color |
| 10.5 | 0.03 | 1 | 0.2 | 98.77 | gradually |
| 13.6 | 0.05 | 1 | 0.2 | 98.75 | deepened from light green to green, and finally showed normal green |

11. Coloring liquids with black color were prepared using raw materials including erbium chloride, ferric chloride neodymium nitrate, polyethylene glycol, citric acid and deionized water. The specific raw material composition and displayed color of the coloring liquids are shown in Table 21 below.

TABLE 21

Composition and displayed color of black coloring liquids

| Erbium chloride Concentration (mmol · L$^{-1}$) | Amt. | Ferric chloride Concentration (mmol · L$^{-1}$) | Amt. | Neodymium nitride Concentration (mmol · L$^{-1}$) | Amt. | Polyethylene glycol | Citric acid | Deionized water | Color |
|---|---|---|---|---|---|---|---|---|---|
| 5.8 | 10 | 7.2 | 0.5 | 4.1 | 2.5 | 1 | 0.2 | 85.8 | The color gradually deepened from light black to black, and finally showed normal black |
| 7.1 | 20 | 8.1 | 1 | 5.4 | 5 | 1 | 0.2 | 72.8 | |
| 12.0 | 40 | 9.6 | 2 | 6.5 | 10 | 1 | 0.2 | 46.8 | |

It can be seen from the coloring liquids prepared in the above tables that with the increase of metal ion concentration, the color of the coloring liquid deepened correspondingly.

Example 9: Adhesive Solution in Method 2

The adhesive solution was prepared according to the above method, with the specific composition shown in Table 22 below.

TABLE 22

Composition of adhesive solutions

| Group | Bis-GMA | Epoxy | MDP | Methacrylate | 4-META | TBHQ | HQ | TBC | Carbon nanotubes | Silicon dioxide | Aluminum oxide | Calcium fluoride | TA | Water |
|---|---|---|---|---|---|---|---|---|---|---|---|---|---|---|
| Group a | 15 | 15 | 15 | 2 | 3 | 2 | 2 | 2 | 30 | 8 | 8 | 8 | 3 | 35 |
| Group b | 15 | 15 | 30 | 2.5 | 3.3 | 2.5 | 2.5 | 2.5 | 35 | 10 | 10 | 10 | 4 | 40 |
| Group c | 15 | 15 | 45 | 3 | 3.6 | 3 | 3 | 3 | 40 | 12 | 12 | 12 | 5 | 45 |
| Group d | 20 | 20 | 20 | 4 | 4 | 4 | 4 | 4 | 45 | 14 | 14 | 14 | 6 | 50 |
| Group e | 20 | 20 | 40 | 5 | 4.3 | 4.5 | 4.5 | 4.5 | 50 | 18 | 18 | 18 | 7 | 55 |
| Group f | 20 | 20 | 60 | 6 | 4.6 | 5 | 5 | 5 | 55 | 20 | 20 | 20 | 8 | 60 |

Note:
In Table 22, the components of the adhesive solution are in parts by weight.

Example 10: Roughening Treatment of Zirconia Base in Method 2

According to the above method, the zirconia ceramic was subjected to surface roughening treatment, totally 18 groups were set, with the specific parameters of each group as shown in Table 23 below, wherein the zirconia denture after surface sandblasting was soaked in 20 mL of the mixed acid solution, and the heating temperature of the mixed acid was 80° C.

TABLE 23

Surface roughening treatment of zirconia denture

| | Surface sandblasting treatment | | | Hot acid treatment | | | |
|---|---|---|---|---|---|---|---|
| Group | Particle size (μm) | Pressure (MPa) | Treatment time (s) | Hydrochloric acid concentration (mol · L$^{-1}$) | Nitric acid concentration (mol · L$^{-1}$) | Volume ratio of hydrochloric acid to nitric acid | Soaking time (min) |
| Group 1 | 30 | 0.2 | 5 | 1 | 1 | 1:2 | 10 |
| Group 2 | 30 | 0.2 | 7 | 1 | 1 | 1:2 | 12.5 |
| Group 3 | 30 | 0.2 | 10 | 1 | 1 | 1:2 | 15 |
| Group 4 | 30 | 0.3 | 5 | 1 | 1 | 1:3 | 10 |
| Group 5 | 30 | 0.3 | 7 | 1 | 1 | 1:3 | 12.5 |
| Group 6 | 30 | 0.3 | 10 | 1 | 1 | 1:3 | 15 |

TABLE 23-continued

Surface roughening treatment of zirconia denture

| | Surface sandblasting treatment | | | Hot acid treatment | | | |
|---|---|---|---|---|---|---|---|
| Group | Particle size (μm) | Pressure (MPa) | Treatment time (s) | Hydrochloric acid concentration (mol · L$^{-1}$) | Nitric acid concentration (mol · L$^{-1}$) | Volume ratio of hydrochloric acid to nitric acid | Soaking time (min) |
| Group 7 | 45 | 0.2 | 5 | 1 | 2 | 1:2 | 10 |
| Group 8 | 45 | 0.2 | 7 | 1 | 2 | 1:2 | 12.5 |
| Group 9 | 45 | 0.2 | 10 | 1 | 2 | 1:2 | 15 |
| Group 10 | 45 | 0.3 | 5 | 1 | 2 | 1:3 | 10 |
| Group 11 | 45 | 0.3 | 7 | 1 | 2 | 1:3 | 12.5 |
| Group 12 | 45 | 0.3 | 10 | 1 | 2 | 1:3 | 15 |
| Group 13 | 60 | 0.2 | 5 | 2 | 1 | 1:2 | 10 |
| Group 14 | 60 | 0.2 | 7 | 2 | 1 | 1:2 | 12.5 |
| Group 15 | 60 | 0.2 | 10 | 2 | 1 | 1:2 | 15 |
| Group 16 | 60 | 0.3 | 5 | 2 | 1 | 1:3 | 10 |
| Group 17 | 60 | 0.3 | 7 | 2 | 1 | 1:3 | 12.5 |
| Group 18 | 60 | 0.3 | 10 | 2 | 1 | 1:3 | 15 |

The treated zirconia dentures in the above groups were soaked in water for 2-5 min, and then air dried for later use.

Example 11: Demonstration of Coloring Effect of One Embodiment of Method 2

A coloring liquid with any one of the colors from Table 11 to Table 21 was selected, mixed with the six groups of adhesive solutions in Table 22, and the color of the mixed solution was adjusted to be consistent with the color of the patient's teeth. Specifically, the color of the coloring liquid can be adjusted by increasing or decreasing the concentration of metal ions, so as to adjust the color of the mixed solution until it is consistent with the color of the patient's teeth. The volume ratio of the adhesive solution to the second coloring liquid was 1:1.

The treated zirconia dentures in Table 23 were colored with the six groups of mixed coloring liquids containing the adhesive solution, that is, the treated zirconia dentures in each group in Table 23 were colored with the six groups of coloring liquids respectively. The coloring results are shown in detail in Table 24 below, wherein the bonding strength refers to the bonding strength between the coloring liquid containing the adhesive solution and the treated zirconia denture. The results showed that the treated zirconia denture in group 7 had the best bonding effect with the zirconia denture after being mixed with the adhesive solution and coloring liquid prepared in group d.

TABLE 24

Coloring results and bonding strength

| Zirconia denture surface roughening treatment group | Adhesive solution group | Effect | Bonding strength between coloring liquid and zirconia denture (MPa) |
|---|---|---|---|
| Group 1 | Group a | After 40 s, the solution painted on or over the surface of zirconia denture began to solidify | 25.62 ± 0.65 |
| | Group b | After 46 s, the solution painted on or over the surface of zirconia denture began to solidify | 27.23 ± 0.15 |
| | Group c | After 52 s, the solution painted on or over the surface of zirconia denture began to solidify | 28.12 ± 0.31 |
| | Group d | After 64 s, the solution painted on or over the surface of zirconia denture began to solidify | 29.69 ± 0.21 |
| | Group e | After 72 s, the solution painted on or over the surface of zirconia denture began to solidify | 29.21 ± 0.17 |
| | Group f | After 82 s, the solution painted on or over the surface of zirconia denture began to solidify | 28.98 ± 0.11 |
| Group 2 | Group a | After 45 s, the solution painted on or over the surface of zirconia denture began to solidify | 25.77 ± 0.31 |
| | Group b | After 52 s, the solution painted on or over the surface of zirconia denture began to solidify | 28.63 ± 0.45 |
| | Group c | After 59 s, the solution painted on or over the surface of zirconia denture began to solidify | 29.31 ± 0.21 |
| | Group d | After 68 s, the solution painted on or over the surface of zirconia denture began to solidify | 30.21 ± 0.55 |
| | Group e | After 78 s, the solution painted on or over the surface of zirconia denture began to solidify | 29.99 ± 0.12 |
| | Group f | After 90 s, the solution painted on or over the surface of zirconia denture began to solidify | 39.45 ± 0.07 |

TABLE 24-continued

Coloring results and bonding strength

| Zirconia denture surface roughening treatment group | Adhesive solution group | Effect | Bonding strength between coloring liquid and zirconia denture (MPa) |
|---|---|---|---|
| Group 3 | Group a | After 48 s, the solution painted on or over the surface of zirconia denture began to solidify | 27.56 ± 0.65 |
| | Group b | After 55 second s, the solution painted on or over the surface of zirconia denture began to solidify | 29.12 ± 0.61 |
| | Group c | After 62 s, the solution painted on or over the surface of zirconia denture began to solidify | 29.66 ± 0.31 |
| | Group d | After 70 s, the solution painted on or over the surface of zirconia denture began to solidify | 30.55 ± 0.54 |
| | Group e | After 81 s, the solution painted on or over the surface of zirconia denture began to solidify | 30.82 ± 0.40 |
| | Group f | After 93 s, the solution painted on or over the surface of zirconia denture began to solidify | 30.45 ± 0.21 |
| Group 4 | Group a | After 55 second s, the solution painted on or over the surface of zirconia denture began to solidify | 29.33 ± 1.02 |
| | Group b | After 58 s, the solution painted on or the surface of zirconia denture began to solidify | 32.18 ± 0.77 |
| | Group c | After 64 s, the solution painted on or over the surface of zirconia denture began to solidify | 32.68 ± 0.36 |
| | Group d | After 71 s, the solution painted on or over the surface of zirconia denture began to solidify | 33.11 ± 0.46 |
| | Group e | After 84 s, the solution painted on or over the surface of zirconia denture began to solidify | 32.99 ± 0.24 |
| | Group f | After 95 s, the solution painted on or over the surface of zirconia denture began to solidify | 31.40 ± 0.17 |
| Group 5 | Group a | After 60 s, the solution painted on or over the surface of zirconia denture began to solidify | 30.61 ± 0.79 |
| | Group b | After 63 s, the solution painted on or over the surface of zirconia denture began to solidify | 32.81 ± 0.65 |
| | Group c | After 65 s, the solution painted on or over the surface of zirconia denture began to solidify | 33.31 ± 0.11 |
| | Group d | After 73 s, the solution painted on or over the surface of zirconia denture began to solidify | 34.78 ± 0.23 |
| | Group e | After 86 s, the solution painted on or over the surface of zirconia denture began to solidify | 35.24 ± 0.45 |
| | Group f | After 98 s, the solution painted on or over the surface of zirconia denture began to solidify | 34.03 ± 0.02 |
| Group 6 | Group a | After 65 s, the solution painted on or over the surface of zirconia denture began to solidify | 31.08 ± 0.73 |
| | Group b | After 68 s, the solution painted on or over the surface of zirconia denture began to solidify | 33.54 ± 0.46 |
| | Group c | After 73 s, the solution painted on or over the surface of zirconia denture began to solidify | 34.06 ± 0.31 |
| | Group d | After 75 s, the solution painted on or over the surface of zirconia denture began to solidify | 35.98 ± 0.25 |
| | Group e | After 89 s, the solution painted on or over the surface of zirconia denture began to solidify | 36.05 ± 0.32 |
| | Group f | After 102 s, the solution painted on or over the surface of zirconia denture began to solidify | 35.44 ± 0.12 |
| Group 7 | Group a | After 72 s, the solution painted on or over the surface of zirconia denture began to solidify | 40.15 ± 0.49 |
| | Group b | After 75 s, the solution painted on or over the surface of zirconia denture began to solidify | 45.12 ± 0.47 |
| | Group c | After 78 s, the solution painted on or over the surface of zirconia denture began to solidify | 47.68 ± 0.10 |
| | Group d | After 81 s, the solution painted on or over the surface of zirconia denture began to solidify | 56.27 ± 0.98 |
| | Group e | After 90 s, the solution painted on or over the surface of zirconia denture began to solidify | 51.82 ± 0.12 |
| | Group f | After 105 s, the solution painted on or over the surface of zirconia denture began to solidify | 48.11 ± 0.47 |
| Group 8 | Group a | After 81 s, the solution painted on or over the surface of zirconia denture began to solidify | 32.56 ± 0.19 |
| | Group b | After 83 s, the solution painted on or over the surface of zirconia denture began to solidify | 34.01 ± 0.37 |
| | Group c | After 85 s, the solution painted on or over the surface of zirconia denture began to solidify | 34.89 ± 0.21 |
| | Group d | After 87 s, the solution painted on or over the surface of zirconia denture began to solidify | 36.56 ± 0.14 |
| | Group e | After 93 s, the solution painted on or over the surface of zirconia denture began to solidify | 36.99 ± 0.11 |
| | Group f | After 107 s, the solution painted on or over the surface of zirconia denture began to solidify | 36.05 ± 0.21 |

TABLE 24-continued

Coloring results and bonding strength

| Zirconia denture surface roughening treatment group | Adhesive solution group | Effect | Bonding strength between coloring liquid and zirconia denture (MPa) |
|---|---|---|---|
| Group 9 | Group a | After 85 s, the solution painted on or over the surface of zirconia denture began to solidify | 32.89 ± 0.22 |
| | Group b | After 88 s, the solution painted on or over the surface of zirconia denture began to solidify | 34.56 ± 0.14 |
| | Group c | After 90 s, the solution painted on or over the surface of zirconia denture began to solidify | 35.06 ± 0.17 |
| | Group d | After 91 s, the solution painted on or over the surface of zirconia denture began to solidify | 36.77 ± 0.21 |
| | Group e | After 96 s, the solution painted on or over the surface of zirconia denture began to solidify | 37.05 ± 0.11 |
| | Group f | After 110 s, the solution painted on or over the surface of zirconia denture began to solidify | 36.66 ± 0.05 |
| Group 10 | Group a | After 90 s, the solution painted on or over the surface of zirconia denture began to solidify | 33.03 ± 0.13 |
| | Group b | After 92 s, the solution painted on or over the surface of zirconia denture began to solidify | 35.05 ± 0.14 |
| | Group c | After 94 s, the solution painted on or over the surface of zirconia denture began to solidify | 35.90 ± 0.33 |
| | Group d | After 96 s, the solution painted on or over the surface of zirconia denture began to solidify | 37.09 ± 0.14 |
| | Group e | After 99 s, the solution painted on or over the surface of zirconia denture began to solidify | 37.93 ± 0.12 |
| | Group f | After 112 s, the solution painted on or over the surface of zirconia denture began to solidify | 38.01 ± 0.01 |
| Group 11 | Group a | After 96 s, the solution painted on or over the surface of zirconia denture began to solidify | 33.76 ± 0.34 |
| | Group b | After 97 s, the solution painted on or over the surface of zirconia denture began to solidify | 35.69 ± 0.37 |
| | Group c | After 99 s, the solution painted on or over the surface of zirconia denture began to solidify | 36.08 ± 0.54 |
| | Group d | After 101 s, the solution painted on or over the surface of zirconia denture began to solidify | 38.07 ± 0.44 |
| | Group e | After 103 s, the solution painted on or over the surface of zirconia denture began to solidify | 38.97 ± 0.34 |
| | Group f | After 113 s, the solution painted on or over the surface of zirconia denture began to solidify | 38.41 ± 0.15 |
| Group 12 | Group a | After 102 s, the solution painted on or over the surface of zirconia denture began to solidify | 34.85 ± 0.69 |
| | Group b | After 103 s, the solution painted on or over the surface of zirconia denture began to solidify | 36.06 ± 0.61 |
| | Group c | After 105 s, the solution painted on or over the surface of zirconia denture began to solidify | 36.97 ± 0.60 |
| | Group d | After 107 s, the solution painted on or over the surface of zirconia denture began to solidify | 39.00 ± 0.37 |
| | Group e | After 110 s, the solution painted on or over the surface of zirconia denture began to solidify | 37.99 ± 0.32 |
| | Group f | After 116 s, the solution painted on or over the surface of zirconia denture began to solidify | 37.06 ± 0.13 |
| Group 13 | Group a | After 88 s, the solution painted on or over the surface of zirconia denture began to solidify | 26.88 ± 0.84 |
| | Group b | After 89 s, the solution painted on or over the surface of zirconia denture began to solidify | 27.48 ± 0.71 |
| | Group c | After 91 s, the solution painted on or over the surface of zirconia denture began to solidify | 28.31 ± 0.70 |
| | Group d | After 93 s, the solution painted on or over the surface of zirconia denture began to solidify | 29.24 ± 0.51 |
| | Group e | After 96 s, the solution painted on or over the surface of zirconia denture began to solidify | 29.98 ± 0.44 |
| | Group f | After 110 s, the solution painted on or over the surface of zirconia denture began to solidify | 28.78 ± 0.11 |
| Group 14 | Group a | After 84 s, the solution painted on or over the surface of zirconia denture began to solidify | 27.09 ± 0.23 |
| | Group b | After 87 s, the solution painted on or over the surface of zirconia denture began to solidify | 28.07 ± 0.54 |
| | Group c | After 89 s, the solution painted on or over the surface of zirconia denture began to solidify | 29.79 ± 0.56 |
| | Group d | After 90 s, the solution painted on or over the surface of zirconia denture began to solidify | 30.88 ± 0.37 |
| | Group e | After 93 s, the solution painted on or over the surface of zirconia denture began to solidify | 30.14 ± 0.08 |
| | Group f | After 105 s, the solution painted on or over the surface of zirconia denture began to solidify | 29.98 ± 0.04 |

TABLE 24-continued

Coloring results and bonding strength

| Zirconia denture surface roughening treatment group | Adhesive solution group | Effect | Bonding strength between coloring liquid and zirconia denture (MPa) |
|---|---|---|---|
| Group 15 | Group a | After 80 s, the solution painted on or over the surface of zirconia denture began to solidify | 28.08 ± 0.66 |
| | Group b | After 84 s, the solution painted on or over the surface of zirconia denture began to solidify | 29.00 ± 0.46 |
| | Group c | After 86 s, the solution painted on or over the surface of zirconia denture began to solidify | 30.15 ± 0.34 |
| | Group d | After 88 s, the solution painted on or over the surface of zirconia denture began to solidify | 31.55 ± 0.30 |
| | Group e | After 91 s, the solution painted on or over the surface of zirconia denture began to solidify | 30.01 ± 0.29 |
| | Group f | After 101 s, the solution painted on or over the surface of zirconia denture began to solidify | 29.66 ± 0.15 |
| Group 16 | Group a | After 76 s, the solution painted on or over the surface of zirconia denture began to solidify | 28.99 ± 0.45 |
| | Group b | After 80 s, the solution painted on or over the surface of zirconia denture began to solidify | 29.74 ± 0.23 |
| | Group c | After 83 s, the solution painted on or over the surface of zirconia denture began to solidify | 31.01 ± 0.21 |
| | Group d | After 86 s, the solution painted on or over the surface of zirconia denture began to solidify | 32.74 ± 0.24 |
| | Group e | After 88 s, the solution painted on or over the surface of zirconia denture began to solidify | 32.09 ± 0.16 |
| | Group f | After 97 s, the solution painted on or over the surface of zirconia denture began to solidify | 31.01 ± 0.16 |
| Group 17 | Group a | After 71 s, the solution painted on or over the surface of zirconia denture began to solidify | 29.47 ± 0.41 |
| | Group b | After 77 s, the solution painted on or over the surface of zirconia denture began to solidify | 30.83 ± 0.45 |
| | Group c | After 80 s, the solution painted on or over the surface of zirconia denture began to solidify | 32.01 ± 0.14 |
| | Group d | After 84 s, the solution painted on or over the surface of zirconia denture began to solidify | 32.97 ± 0.24 |
| | Group e | After 86 s, the solution painted on or over the surface of zirconia denture began to solidify | 32.06 ± 0.10 |
| | Group f | After 93 s, the solution painted on or over the surface of zirconia denture began to solidify | 31.62 ± 0.01 |
| Group 18 | Group a | After 64 s, the solution painted on or over the surface of zirconia denture began to solidify | 30.15 ± 0.59 |
| | Group b | After 74 s, the solution painted on or over the surface of zirconia denture began to solidify | 31.26 ± 0.49 |
| | Group c | After 79 s, the solution painted on or over the surface of zirconia denture began to solidify | 32.88 ± 0.47 |
| | Group d | After 81 s, the solution painted on or over the surface of zirconia denture began to solidify | 33.65 ± 0.40 |
| | Group e | After 83 s, the solution painted on or over the surface of zirconia denture began to solidify | 32.98 ± 0.18 |
| | Group f | After 89 s, the solution painted on or over the surface of zirconia denture began to solidify | 32.01 ± 0.11 |
| control group | Group a | After 34 s, the solution painted on or over the surface of zirconia denture began to solidify | 20.18 ± 0.89 |
| | Group b | After 37 s, the solution painted on or over the surface of zirconia denture began to solidify | 22.34 ± 0.75 |
| | Group c | After 42 s, the solution painted on or over the surface of zirconia denture began to solidify | 23.56 ± 0.44 |
| | Group d | After 46 s, the solution painted on or over the surface of zirconia denture began to solidify | 24.12 ± 0.24 |
| | Group e | After 50 s, the solution painted on or over the surface of zirconia denture began to solidify | 23.31 ± 0.13 |
| | Group f | After 53 s, the solution painted on or over the surface of zirconia denture began to solidify | 22.03 ± 0.10 |

Example 12: Demonstration of Coloring Method of Another Embodiment of Method 2

In another embodiment of Method 2, the second coloring liquid is not mixed with the adhesive solution. First, the zirconia base after surface roughening treatment is colored with the second coloring liquid. When the color of the zirconia base is observed to be consistent with that of the patient's teeth, coloring is stopped, the zirconia base is oven-dried and then soaked in the adhesive solution for 1-20 min, so that the adhesive solution seals the coloring liquid in the pores of the zirconia and fills the pores on the surface of the zirconia to form a protective film on or over the surface of the zirconia ceramic, which prevents bacteria, enzymes and other substances in the oral cavity from entering the pores and causing infection and other hazards. Finally, the zirconia base is taken out, put into a denture sintering furnace, heated up to 1530° C. at a rate of 5° C./min, kept at this temperature for crystallization for 120 min, and then cooled down along with the furnace.

What is claimed is:
1. A zirconia treatment method, comprising:
(1) color masking a zirconia ceramic prepared by pre-sintering zirconia powder;
(2) after color masking the zirconia ceramic, surface roughening the zirconia ceramic;
(3) after surface roughening the zirconia ceramic, coloring the zirconia ceramic; and
(4) carrying out surface protection treatment on the zirconia ceramic;
wherein color masking comprises painting a color masking liquid on or over a surface of the zirconia ceramic, oven-drying the painted zirconia ceramic, then sintering the dried, painted zirconia ceramic.

2. The zirconia treatment method according to claim 1, wherein the color masking liquid has a formula comprising, in mass percentages, 95-98% of a mother liquor, 1.3-1.6% of an alcohol, 0.03-3.40% of potassium nitrate, 0.1-0.3% of yttrium chloride and 0.3-0.4% of citric acid; and
the mother liquor has a formula comprising, in mass percentages, 18-23% of ethylene glycol, 1-5% of gluconic acid, 1-3% of citric acid, 1-3% of praseodymium nitrate, and water.

3. The zirconia treatment method according to claim 1, wherein sintering is carried out at 1530° C. for 2 h.

4. The zirconia treatment method according to claim 1, wherein the zirconia ceramic is colored with a first coloring liquid comprising, in mass percentages, 0.01-26% of a first coloring agent, 0.2-35% of a first dispersant and 60-97% of a first solvent.

5. The zirconia treatment method according to claim 4, wherein the first coloring agent is at least one of erbium chloride, ferric chloride and manganese nitrate; and/or the first dispersant is a polyethylene glycol.

6. The zirconia treatment method according to claim 5, wherein the mass percentage of the polyethylene glycol is 10%.

7. The zirconia treatment method according to claim 5, wherein the first coloring agent is erbium chloride, ferric chloride and manganese nitrate, in mass percentages of 0.5-13%, 0.5-6% and 0.01-6%, respectively.

8. The zirconia treatment method according to claim 1, wherein the zirconia ceramic is colored with a second coloring liquid comprising, by mass percentages, 0.01-48% of a second coloring agent, 0.1-5% of a second dispersant, 0.05-2% of a complexing agent and 45-99% of a second solvent.

9. The zirconia treatment method according to claim 8, wherein the second coloring agent is one or a mixture of two or more of erbium chloride, ferric chloride, neodymium nitrate, manganese nitrate, ammonium metavanadate, cerium nitrate, praseodymium nitrate, cobalt nitrate and nickel nitrate; and/or the second dispersant is any one of a polyethylene glycol, a polyacrylic acid or a polyurethane; and/or the complexing agent is any one of citric acid, glucose, ethylenediaminetetraacetic acid, sodium citrate or 2,3-dimercaptosuccinic acid.

10. The zirconia treatment method according to claim 1, wherein the surface protection treatment comprises using an adhesive solution comprising, in parts by mass, 40-100 parts of a matrix, 2-6 parts of a diluent, 3-5 parts of an adhesive monomer, 6-15 parts of a polymerization inhibitor, 30-55 parts of carbon nanotubes, 20-60 parts of a filler, 1-8 parts of tartaric acid and 30-70 parts of water.

11. The zirconia treatment method according to claim 1, wherein surface roughening comprises:
(1) sandblasting the zirconia ceramic using 30-60 μm zirconia powder for 5-10 s under a pressure of 0.2-0.3 MPa; and then washing the sandblasted zirconia ceramic 3-5 times with deionized water;
(2) mixing hydrochloric acid and nitric acid, wherein the hydrochloric acid has a concentration of 1-2 mol/L, the nitric acid has a concentration of 1-2 mol/L, and the volume ratio of hydrochloric acid to nitric acid is 1:2-3; heating the mixed hydrochloric acid and nitric acid to 70-80° C. to obtain a mixed acid solution; and soaking the sandblasted zirconia ceramic in the mixed acid solution for 10-15 min; and
(3) washing the acid-soaked zirconia ceramic 3-5 times with deionized water.

12. The zirconia treatment method according to claim 1, further comprising forming a protective film on or over the surface of the zirconia ceramic after the surface protection treatment.

13. A zirconia treatment method, comprising:
(1) color masking a zirconia ceramic prepared by pre-sintering zirconia powder;
(2) coloring the zirconia ceramic; and
(3) carrying out surface protection treatment on the zirconia ceramic;
wherein color masking comprises painting a color masking liquid on or over a surface of the zirconia ceramic, oven-drying the painted zirconia ceramic, then sintering the dried, painted zirconia ceramic, and the surface protection treatment comprises using an adhesive solution comprising, in parts by mass, 40-100 parts of a matrix, 2-6 parts of a diluent, 3-5 parts of an adhesive monomer, 6-15 parts of a polymerization inhibitor, 30-55 parts of carbon nanotubes, 20-60 parts of a filler, 1-8 parts of tartaric acid and 30-70 parts of water.

14. The zirconia treatment method according to claim 13, wherein coloring and carrying out the surface protection treatment are performed simultaneously, and
using the adhesive solution comprises:
mixing a coloring liquid with the adhesive solution to obtain a mixed solution, painting the mixed solution on or over the surface of the zirconia ceramic, and crystallizing the painted zirconia ceramic at a high temperature; or
painting the adhesive solution on or over the surface of the zirconia ceramic after coloring the zirconia ceramic, and then drying the painted, colored zirconia ceramic.

15. The zirconia treatment method according to claim 13, wherein the diluent is a methacrylate; and/or the adhesive monomer is 4-methacryloyloxyethyl trimellitic anhydride; and/or the polymerization inhibitor is one or a mixture of two or more of tert-butyl hydroquinone, hydroquinone and p-tert-butyl catechol.

16. The zirconia treatment method according to claim 13, wherein the filler is a mixture of two or more of silicon dioxide, aluminum oxide, calcium fluoride and titanium dioxide.

17. The zirconia treatment method according to claim 16, comprising melting the filler, mixing and quenching the melted filler, and then crushing the mixed and quenched filler to a particle size smaller than that of the carbon nanotubes.

18. The zirconia treatment method according to claim 13, wherein the color masking liquid has a formula comprising, in mass percentages, 95-98% of a mother liquor, 1.3-1.6% of an alcohol, 0.03-3.40% of potassium nitrate, 0.1-0.3% of yttrium chloride and 0.3-0.4% of citric acid; and the mother liquor has a formula comprising, in mass percentages, 18-23% of ethylene glycol, 1-5% of gluconic acid, 1-3% of citric acid, 1-3% of praseodymium nitrate, and water.

19. A zirconia treatment method, comprising:
(1) color masking a zirconia ceramic prepared by pre-sintering zirconia powder;
(2) coloring the zirconia ceramic;
(3) carrying out surface protection treatment on the zirconia ceramic; and
(4) forming a protective film on or over the surface of the zirconia ceramic after the surface protection treatment;
wherein color masking comprises painting a color masking liquid on or over a surface of the zirconia ceramic, oven-drying the painted zirconia ceramic, then sintering the dried, painted zirconia ceramic, and forming the protective film comprises painting a layer of a silane coupling agent on or over the surface of the zirconia ceramic, and then drying the painted zirconia ceramic.

20. The zirconia treatment method according to claim 19, further comprising surface roughening the zirconia ceramic before coloring the zirconia ceramic and after color masking the zirconia ceramic.

* * * * *